US009839380B2

(12) United States Patent
Short et al.

(10) Patent No.: US 9,839,380 B2
(45) Date of Patent: *Dec. 12, 2017

(54) PHENOTYPIC INTEGRATED SOCIAL SEARCH DATABASE AND METHOD

(71) Applicant: iPhenotype LLC, San Diego, CA (US)

(72) Inventors: Jay M. Short, Del Mar, CA (US); Steve Briggs, Del Mar, CA (US)

(73) Assignee: IPHENOTYPE LLC, San Diego, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 14/892,185

(22) PCT Filed: May 23, 2014

(86) PCT No.: PCT/US2014/039281
§ 371 (c)(1),
(2) Date: Nov. 18, 2015

(87) PCT Pub. No.: WO2014/190230
PCT Pub. Date: Nov. 27, 2014

(65) Prior Publication Data
US 2016/0110524 A1    Apr. 21, 2016

Related U.S. Application Data

(63) Continuation-in-part of application No. PCT/US2013/042527, filed on May 23, 2013.
(Continued)

(51) Int. Cl.
| | |
|---|---|
| G01N 33/53 | (2006.01) |
| A61B 5/145 | (2006.01) |
| G06F 19/18 | (2011.01) |
| G06F 19/00 | (2011.01) |
| G06Q 30/02 | (2012.01) |
| G06Q 50/22 | (2012.01) |
| G06F 17/30 | (2006.01) |
| A61B 3/113 | (2006.01) |
| A61B 5/0205 | (2006.01) |
| A61B 5/0488 | (2006.01) |
| A61B 5/1459 | (2006.01) |
| A61B 5/1473 | (2006.01) |
| A61B 5/00 | (2006.01) |
| G09B 19/00 | (2006.01) |
| A61B 5/16 | (2006.01) |
| G06Q 30/06 | (2012.01) |

(Continued)

(52) U.S. Cl.
CPC .......... *A61B 5/14546* (2013.01); *A61B 3/113* (2013.01); *A61B 5/02055* (2013.01); *A61B 5/0488* (2013.01); *A61B 5/1459* (2013.01); *A61B 5/1473* (2013.01); *A61B 5/165* (2013.01); *A61B 5/4875* (2013.01); *A61B 5/7246* (2013.01); *G06F 17/30598* (2013.01); *G06F 17/30867* (2013.01); *G06F 19/18* (2013.01); *G06F 19/3406* (2013.01); *G06F 19/3443* (2013.01); *G06F 19/363* (2013.01); *G06Q 30/02* (2013.01); *G06Q 30/0631* (2013.01); *G06Q 50/22* (2013.01); *G09B 5/12* (2013.01); *G09B 19/00* (2013.01); *A61B 5/021* (2013.01); *A61B 5/024* (2013.01); *A61B 5/05* (2013.01); *A61B 5/0816* (2013.01); *G06F 19/24* (2013.01)

(58) Field of Classification Search
None
See application file for complete search history.

(56) References Cited

U.S. PATENT DOCUMENTS

| | | |
|---|---|---|
| 4,433,051 A | 2/1984 | Gilad et al. |
| 4,436,586 A | 3/1984 | Elmore |

(Continued)

FOREIGN PATENT DOCUMENTS

| | | |
|---|---|---|
| EP | 0232967 A2 | 8/1987 |
| WO | WO9615270 A1 | 5/1996 |

(Continued)

OTHER PUBLICATIONS

CINGA (2000).*
Liu et al. (Int. J. Nurs Stud 2011 vol. 48, p. 904-913).*
European Search Report; dated Dec. 15, 2106 for EP Application No. 14801639.7.
Leung, Y. F., & Cavalieri, D. (2003). Fundamentals of cDNA microarray data analysis. TRENDS in Genetics, 19(11), 649.
Wright et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures", Prostate Cancer and Prostatic Diseases, 2:264-76, 1999.
Cravatt, B. F., & Sorensen, E. J. (2000). Chemical strategies for the global analysis of protein function. Current opinion in chemical biology, 4(6), 663-668.

(Continued)

*Primary Examiner* — Changhwa J Cheu
(74) *Attorney, Agent, or Firm* — Mendelsohn Dunleavy, P.C.

(57) ABSTRACT

A method for generating correlations between human biological phenotype and human behavioral and/or emotional phenotype, and optionally to temporal location, comprising the steps of correlating data on biological phenotype with survey-based data on behavioral and/or emotional phenotype. The data on biological phenotype is collected from a sample from an individual, and the survey-based data can be collected from answers to behavioral and emotional questions from the individual or from observations of the individual by a third party. Correlations can further be used to predict behavior, including preferences, wellness needs and desires, and/or emotions. Feedback, advice and guidance can be provided to individuals based on such correlations. Such correlations are further useful for product and service providers and industries for purposes of standardizing or rating product quality and efficacy, and/or for promotion and selling purposes. A database comprising the data on biological phenotype and survey-based data is also provided.

4 Claims, No Drawings

Related U.S. Application Data

(60) Provisional application No. 61/909,378, filed on Nov. 27, 2013, provisional application No. 61/909,873, filed on Nov. 27, 2013, provisional application No. 61/909,386, filed on Nov. 27, 2013, provisional application No. 61/895,964, filed on Oct. 25, 2013, provisional application No. 61/895,969, filed on Oct. 25, 2013, provisional application No. 61/895,974, filed on Oct. 25, 2013.

(51) Int. Cl.
  *G09B 5/12* (2006.01)
  *G06F 19/24* (2011.01)
  *A61B 5/021* (2006.01)
  *A61B 5/024* (2006.01)
  *A61B 5/08* (2006.01)
  *A61B 5/05* (2006.01)

(56) References Cited

U.S. PATENT DOCUMENTS

| | | |
|---|---|---|
| 4,591,570 A | 5/1986 | Chang |
| 4,829,010 A | 5/1989 | Chang |
| 5,100,777 A | 3/1992 | Chang |
| 5,270,163 A | 12/1993 | Gold et al. |
| 5,475,096 A | 12/1995 | Gold et al. |
| 5,772,874 A | 6/1998 | Quinn et al. |
| 5,795,469 A | 8/1998 | Quinn et al. |
| 5,919,368 A | 7/1999 | Quinn et al. |
| 5,925,517 A | 7/1999 | Tyagi et al. |
| 5,968,367 A | 10/1999 | Quinn et al. |
| 6,103,476 A | 8/2000 | Tyagi et al. |
| 6,107,623 A | 8/2000 | Bateman et al. |
| 6,124,137 A | 9/2000 | Hutchens et al. |
| 6,127,134 A | 10/2000 | Minden et al. |
| 6,150,097 A | 11/2000 | Tyagi et al. |
| 6,204,500 B1 | 3/2001 | Whitehouse et al. |
| 6,268,144 B1 | 7/2001 | Koster |
| 6,911,308 B2* | 6/2005 | Shuber .............. C12Q 1/689 435/6.13 |
| 7,468,034 B2 | 12/2008 | Ouchi |
| 8,200,525 B2 | 6/2012 | Kilger et al. |
| 9,316,651 B2* | 4/2016 | Kalns ............. G01N 33/6848 |
| 9,442,121 B2* | 9/2016 | Kawamura ....... G01N 33/6893 |
| 2003/0045827 A1 | 3/2003 | Nier et al. |
| 2003/0083822 A2 | 5/2003 | Brunner et al. |
| 2004/0019435 A1 | 1/2004 | Winfield et al. |
| 2008/0033819 A1 | 2/2008 | Leschly |
| 2009/0042206 A1 | 2/2009 | Schneider et al. |
| 2009/0104615 A1 | 4/2009 | Godfrey et al. |
| 2010/0113892 A1 | 5/2010 | Kaput et al. |
| 2011/0224912 A1 | 9/2011 | Bhavaraju et al. |
| 2011/0230732 A1 | 9/2011 | Edman et al. |
| 2012/0072233 A1 | 3/2012 | Hanlon et al. |
| 2012/0094315 A1* | 4/2012 | Fryar-Williams .. G01N 33/6896 435/7.92 |
| 2012/0130732 A1 | 5/2012 | Blander et al. |
| 2012/0301882 A1 | 11/2012 | Koster et al. |

FOREIGN PATENT DOCUMENTS

| | | |
|---|---|---|
| WO | WO0011208 A1 | 3/2000 |
| WO | WO0065472 A1 | 11/2000 |
| WO | WO2013018070 A1 | 2/2013 |

OTHER PUBLICATIONS

Gygi, Steven P., et al. "Evaluation of two-dimensional gel electrophoresis-based proteome analysis technology." Proceedings of the National Academy of Sciences 97.17 (2000): 9390-9395.

Jagannath, Aarti, et al. "The CRTC1-SIK1 pathway regulates entrainment of the circadian clock." Cell 154.5 (2013): 1100-1111.

Pettersson, Erik, Joakim Lundeberg, and Afshin Ahmadian. "Generations of sequencing technologies." Genomics 93.2 (2009): 105-111.

Shalon, Dari, Stephen J. Smith, and Patrick O. Brown. "A DNA microarray system for analyzing complex DNA samples using two-color fluorescent probe hybridization." Genome research 6.7 (1996): 639-645.

Brown, Patrick O. "Quantitative Monitoring of Gene Expression Patterns with a Complementary DNA Microarray." Science 270 (1995): 467.

Pease, A. Caviani, et al. "Light-generated oligonucleotide arrays for rapid DNA sequence analysis." Proceedings of the National Academy of Sciences 91.11 (1994): 5022-5026.

Saiki, Randall K., et al."Enzymatic amplification of beta-globin genomic sequences and restriction site analysis for diagnosis of sickle cell anemia." Science 230.4732 (1985): 1350-1354.

Ebstein, Richard P., et al. "Genetics of Human Social Behavior." Neuron 65 (2010).

Northen, Trent R., et al. "Clathrate nanostructures for mass spectrometry." Nature 449.7165 (2007): 1033-1036.

Bouatra, Souhaila, et al. "The human urine metabolome." PloS one 8.9 (2013): e73076.

Kandel, Denise B., et al. "Urine nicotine metabolites and smoking behavior in a multiracial/multiethnic national sample of young adults." American Journal of Epidemiology 165.8 (2007): 901-910.

"Gut feelings: the future of psychiatry may be inside your stomach," available at http://www.theverge.com/2013/8/12/4595712/gut-feelings-the-future-of-psychiatry-may-beinside-your-stomach, 2013.

Xia, Fan, et al. "Colorimetric detection of DNA, small molecules, proteins, and ions using unmodified gold nanoparticles and conjugated polyelectrolytes." PNAS 107.24 (2010): 10837-10841.

Opportunities in Neuroscience for Future Army Applications (2009) Board on Army Science and Technology (BAST), Committee on Opportunities in Neuroscience for Future Army Applications; Division on Engineering and Physical Sciences; National Research Council of The National Academies, The National Academies Press, Washington, D.C. www.nap.edu.

Greenfieldboyce, N., "Fat Bacteria in Human Guts Tied to Obesity," Dec. 20, 2006; Retrieved from http://www.npr.org/templates/story/story.php?storyId=6654607.

Zhang, Yian-Biao, et al. "Functionalized Carbon Nanotubes for Detecting Viral Proteins." Nano Lett 7.10 (2007): 3087.

De Ruiter, J. R., "Genetic Markers in Primate Studies: Elucidating Behavior and its Evolution," International Journal of Primatology, 25 (5), (2004). pp. 1173-1189.

CN Office Action; dated Jul. 6, 2017 for CN Application No. CN 201480029773.0.

\* cited by examiner

PHENOTYPIC INTEGRATED SOCIAL SEARCH DATABASE AND METHOD

BACKGROUND OF THE INVENTION

1. Field of the Invention

The present invention relates to correlating biological phenotype with behavior and emotions. In particular, the present invention provides methods and databases for relating social behavior and emotions to biological phenotype.

2. Description of the Related Technology

There is an enormous interest in understanding and predicting consumer behavior. For example, many online retailers have used consumer browsing history to find out in which merchants the consumer is interested and from which the consumer may buy. As a result, targeted advertisement may be directed at the consumer for recommending suitable merchants. Several groups have used user feedback to correlate preferences for products, activities, and beliefs (for example, Hunch: www.hunch.com). Others have used shopping behavior as a guide to recommend future product purchases (e.g. Amazon). Other specialized programs ("apps") for devices include software that gathers and compares data for similar users for future prediction. One example is restaurant apps, where users rate restaurants and data is collected and used for prediction of future restaurant choices.

Methods of predicting consumer behavior have also been described. For example, U.S. Pat. No. 8,200,525, which is hereby incorporated herein by reference in its entirety, describes a process and system for predicting consumer behavior by combining converted information from disparate databases including, for example, consumer transactional information.

The ability to predict future purchasing choices is highly desirable in order to allow sellers to be able to locate likely consumers during a purchase cycle. With the right information, merchants can achieve customized, targeted advertising and offer incentives to the right customers (e.g. discount coupons). It is also widely recognized that consumers desire to identify, via search of online inventories, exactly what they want quickly, easily and with mobile devices. Making searches more efficient also engages users and provides them with significant added value. Traditionally, quantitative physical biological parameters are not used for understanding human behaviors or shopping experiences.

Several groups have used genetic fragments such as single-nucleotide polymorphisms (SNPs) or DNA sequence variations that occur when a single nucleotide—A, T, C or G—in the genome or other shared sequence differs between members of a biological species or paired chromosomes in an individual). Questionnaires can be used to correlate health risks in individuals with their genetic variations, as well as to determine genealogy of individuals (for example, 23 and Me, National Geographic and WorldFamilies.net). Further, many companies use genetic information to diagnose disease, including mental conditions.

Examples of measurement of biological molecules to diagnose medical conditions include tests such as the widely available pregnancy tests and other over the counter assays available to consumers and medical laboratories; yet these examples do not specifically describe or predict behavior, a feature that is desirable for merchants and consumers.

US 2003/0083822 A2 discloses a method for determining drug effects based on correlating animal biological phenotype with animal behavior after ingesting a drug, comprising: (i) obtaining behavioral and physiological measurements, and one or more of neurological and biochemical measurements, for one or more animals treated with a test compound; (ii) comparing the obtained data with a signature that represents a probability relationship between a response of an animal to a test compound and a set of predictor variables which define correlations between observed behavioral, neurological, biochemical and/or physiological responses and known drugs and/or predetermined genetic traits. The relationship may be derived through using at least one automated non-linear algorithm. Finally, from the comparison data of step (ii), the suitability for further clinical development of the test compound is determined.

US 2011/0224912 discloses a method for quantifying the effect of a medication on a patient. The method comprises the steps of: providing a monitoring platform capable of measuring one or more physiological parameters; obtaining a first set of measurements of the physiological parameters from the patient by using the monitoring platform; compiling a first signature from the first set of measurements; and comparing the first signature with a second signature compiled previously to determine the probability of a change in the physiological parameter.

US 2011/0230732 discloses a system for monitoring physiological conditions of an individual to enable responses (e.g. feedback, recommendations, rewards or guidance) to be presented to the individual within the context of electronic media. The system comprises at least one monitor enabling the measurement of at least one physiological parameter associated with the health status or change of health status of said individual and at least one evaluator that is contained substantially within at least one electronic device. The evaluator can receive physiological data from the monitor and determine the health status or a change in health status of the individual. At least one response is generated by at least one evaluator, based upon a comparison of the determined status to current, past, comparative, or stored physiological data. The response may be conveyed to the individual via electronic media for the purpose of improving the health of said individual.

U.S. Pat. No. 7,468,034 B2 discloses a method of monitoring the posture of a clothed subject by acquiring information on positional displacements of the surface of the subject's body, and computationally determining the posture changes of the positional displacements of the surface of the subject's body. Some limited emotional conditions may be inferred from the posture information, such as a degree of relaxation, a degree of stress or a state of joy or anger of the person. The patent also discloses that, based on the inferred emotional conditions, recommendations may be made to the person for assisting the person, such as choice of music.

The present invention provides a method for correlating human biological parameters with human behavior and/or emotional states, and optionally to temporal location. Such correlations will enable adaptation of the living environment and lifestyle of the individual, by, for example, suggesting activities, products, services, etc. to the individual based on predicted behavior and/or emotional states. Correlations can further be used to predict behavior, including preferences, wellness needs and desires, and/or emotions. Feedback, advice and guidance can be provided to individuals based on such correlations. Such correlations are further useful for product and service providers and industries for purposes of standardizing or rating product quality and efficacy, and/or for promotion and selling purposes.

SUMMARY OF THE INVENTION

In one aspect, the present invention provides a method for generating correlations between biological phenotype and behavioral/emotional phenotype, comprising the steps of: correlating data on a biological phenotype data collected from an individual with a behavioral and/or emotional phenotype, where the biological phenotype is indicated by one or more biomarkers in a sample.

In another aspect, the method of the present invention may also use data on physiological phenotype of the individual, in combination with the data on a biological phenotype of the individual to generate correlations between a biological and/or physiological phenotype and a behavioral and/or emotional phenotype.

In another aspect, the method of the present invention may also use data on temporal location of the individual, in combination with the data on a biological phenotype of the individual to generate correlations between a biological phenotype and a behavioral and/or emotional phenotype and/or temporal location.

In yet another aspect, the present invention provides a database comprising data on a biological phenotype of a subject, data on a behavioral and/or emotional phenotype of the subject, and correlations between a biological phenotype and a behavioral and/or emotional phenotype.

In yet another aspect, the database of the present invention may comprise the identity of the subject.

In yet another aspect, the database of the present invention may comprise the time and/or location that the sample is collected from the subject and the correlations in the database are based, at least in part, on time and/or location information.

In aspects of the present invention, behavior is lifestyle behavior, including preferences, wellness needs, deviations from wellness, personality traits and/or desires, and data is collected in an undirected way.

Correlations of the present invention are used for many applications, including but not limited to: to provide feedback or guidance to an individual, including a consumer; to provide information to a product provider useful in marketing and selling of products or services; and to provide industry information useful in grading of products or services.

DEFINITIONS

The term "sample" as used herein refers to bodily fluid or other materials taken from the body, including but not limited to saliva, sweat, blood, tears, mucus, urine, mouth cell scrapings, stool, breath, fart gas, hair follicle, fingernails, or other bodily cells. Samples can be collected by having an individual breathing onto a surface, scraping a check, spitting into a tube, urinating into a or onto a container or surface, or providing a fluid (liquid) or solid sample by any other method whereby the sample can be collected for analysis, for example using a sampling device.

The term "body fluid" as used herein refers to any fluid that can be isolated from the body of an individual. For example, "body fluid" may include blood, plasma, serum, bile, saliva, urine, tears, perspiration, pheromones and the like. The body fluids of interest include fluids excreted by the body, such as urine, lacrimal fluid, sputum and nasal secretion, but also internal body fluids, such as lymph, synovial fluid (obtained by arthrocentesis) or cerebrospinal fluid (obtained by lumbar puncture).

The term "database" as used herein refers to an organized collection of data. The data are typically organized to model relevant aspects of reality in a way that supports processes requiring this information.

The term "phenotype" as used herein includes traits or characteristics that can be made visible by some technical procedure, and can include behavior as an observable characteristic. The phenotype of the present invention may include a biological phenotype based on biological parameters of physical biological components of an individual and behavioral and/or emotional phenotypes based on behaviors or emotional states of an individual or combinations thereof.

The term "polypeptide" as used herein refers to a polymer of amino acids joined by peptide bonds. Natural polypeptides are long, continuous and unbranched peptide chains. A polypeptide may be a protein, or a fragment of a protein. A polypeptide may have one or more modifications, such as a post-translational modification (e.g., glycosylation, etc.) or any other modification (e.g., pegylation, etc.).

The term "proteome" as used herein is an entire set of proteins expressed by a genome, cell, tissue or organism at a certain time. More specifically, it is the set of expressed proteins in a given type of cell or organism, at a given time, under defined conditions.

The terms "polynucleotide," "nucleic acid" and "nucleic acid molecule" are used interchangeably herein to mean a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, as well as any other type of polynucleotide which is an N- or C-glycoside of a purine or pyrimidine base.

The terms "nucleoside" and "nucleotide" as used herein include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen or aliphatic groups, or are functionalized as ethers, amines, or the like. The term "nucleotidic unit" is intended to encompass nucleosides and nucleotides.

The term "microbes" as used herein includes virus, prokaryotic and eukaryotic microbial species from the Domains Archaea, Bacteria and Eucarya, the latter including yeast and filamentous fungi, protozoa, algae, or higher Protista. The terms "microbial cells" and "microorganism" are used interchangeably with the term "microbes."

The term "microflora" as used herein refers a population of microbes in a specific localized location. Examples of microflora include the microbes in the stomach, microbes in an intestine, microbes colonizing the outer surface of normal skin. Microflora do not typically pose a threat to the individual under normal circumstances, and do not cause infection.

The term "metabolite" as used herein refers to any substance produced during metabolism. The term "metabolism" as used herein is defined as all chemical reactions involved in maintaining the living state of the cells and the organism.

Metabolism can be conveniently divided into two categories: catabolism which is the breakdown of molecules to obtain energy and anabolism which is the synthesis of all compounds needed by the cells. Metabolism is closely linked to nutrition and the availability of nutrients.

The term "aptamer" as used herein refers to a nucleic acid that has a specific binding affinity for a target molecule, such as a protein, polynucleotide or a small molecule (e.g. metabolite). Aptamers may be single or double-stranded nucleic acids (such as RNA or DNA) whose distinct nucleotide sequence determines the folding of the molecule into a unique three dimensional structure. Like all nucleic acids, a particular nucleic acid ligand may be described by a linear sequence of nucleotides (A, U, T, C and G), typically 15-40 nucleotides long.

The term "array" as used herein includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins or antibodies), carbohydrates, lipids, aptamers, etc.) associated with that region. In many embodiments of interest, the arrays are arrays of nucleic acids, including oligonucleotides, polynucleotides, cDNAs, mRNAs, synthetic mimetics thereof, and the like. Where the arrays are arrays of oligonucleotides, the oligonucleotides may be covalently attached to the arrays at any point along the nucleic acid chain. In some embodiments, the oligonucleotides are attached at one of their termini (e.g. the 3' or 5' terminus).

In some embodiments, arrays may comprise a plurality of antibodies, and/or aptamers which selectively bind to molecules (e.g., polynucleotides, polypeptides, metabolites) in a sample.

The term "microarray" as used herein refers to polynucleotide, polypeptide, aptamer and chemical microarrays. Specific polynucleotides, polypeptides, antibodies, small molecule compounds, aptamer, peptides, and carbohydrates may be immobilized on solid surfaces to form microarrays. Microarrays may be used to detect polynucleotide, polypeptide and other chemicals in a sample.

The term "specific" "specifically" or "specificity" as used herein refers to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc.

The term "antibody", as used herein, refers to intact immunoglobulin molecules, as well as fragments of immunoglobulin molecules, such as Fab, Fab', (Fab')2, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

The term "single-chain antibody" as used herein refers to a polypeptide comprising a VH domain and a VL domain in polypeptide linkage, generally liked via a spacer peptide (e.g., [Gly-Gly-Gly-Gly-Ser]x), and which may comprise additional amino acid sequences at the amino- and/or carboxy-termini. For example, a single-chain antibody may comprise a tether segment for linking to the encoding polynucleotide. As an example a scFv is a single-chain antibody. Single-chain antibodies are generally proteins consisting of one or more polypeptide segments of at least 10 contiguous amino substantially encoded by genes of the immunoglobulin superfamily (e.g., see Williams and Barclay, 1989, pp. 361-368, which is incorporated herein by reference), most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The term "amino acid" as used herein refers to any organic compound that contains an amino group ($-NH_2$) and a carboxyl group ($-COOH$); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gin or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" as used herein refers that the number of copies of a polynucleotide is increased.

The term "polymerase chain reaction (PCR)" as used herein refers to a system for in vitro amplification of DNA. Two synthetic oligonucleotide primers, which are complementary to two regions of the target DNA (one for each strand) to be amplified, are added to the target DNA (that need not be pure), in the presence of excess deoxynucleotides and a heat-stable DNA polymerase, e.g., Taq DNA polymerase. In a series, e.g., 30, of temperature cycles, the target DNA is repeatedly denatured (e.g., around 90° C.), annealed to the primers (e.g., at 50-60° C.) and a daughter strand extended from the primers (e.g., 72° C.). As the daughter strands themselves act as templates for subsequent cycles, DNA fragments matching both primers are amplified exponentially, rather than linearly.

The term "nested PCR" as used herein refers to a PCR in which specificity is improved by using two sets of primers sequentially. An initial PCR is performed with the "outer" primer pairs, then a small aliquot is used as a template for a second round of PCR with the "inner" primer pair.

The term "reverse transcription PCR or RT-PCR" as used herein refers to PCR in which the starting template is RNA, implying the need for an initial reverse transcriptase step to make a DNA template. Some thermostable polymerases have appreciable reverse transcriptase activity; however, it is more common to perform an explicit reverse transcription, inactivate the reverse transcriptase or purify the product, and proceed to a separate conventional PCR.

The term "primer" as used herein refers to an oligonucleotide that hybridizes to a target sequence, typically to prime the nucleic acid in the amplification process.

The term "oligonucleotide" (or synonymously an "oligo") as used herein refers to either a single stranded polydeoxynucleotide or two complementary polydeoxynucleotide strands which may be chemically synthesized. Such synthetic oligonucleotides may or may not have a 5' phosphate.

The terms "nucleic acid probe" as used herein refers to a structure comprising a polynucleotide, as defined above that contains a nucleic acid sequence that can bind to a corresponding target. The polynucleotide regions of probes may be composed of DNA, and/or RNA, and/or synthetic nucleotide analogs.

The term "sequence identity" as used herein means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence.

The term "complementary or matched" as used herein means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s). The percentage of sequence identity or homology is calculated by comparing one to another when aligned to corresponding portions of the reference sequence.

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a nonspecific protein can be described as specifically binding to the antigen. (Similarly, a nucleic acid probe can be described as specifically binding to a nucleic acid target if it forms a specific duplex with the target by base pairing interactions (see above).).

The term "assay" as used herein, is a measurement to quantify or qualify a component in a sample, preferably a polypeptide, polynucleotide, metabolite, or other biological molecule. One or more polypeptides and/or the entire proteome of cells in a sample from an individual may be assayed.

The term "detect" or "detection" as used herein refers to the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified.

The term "target" as used herein is an analyte of interest. The term "analyte" refers to a substance, compound or component whose presence or absence in a sample has to be detected. Analytes include but are not limited to biomolecules and in particular biomarkers. The term "biomolecule" as used herein indicates a substance compound or component associated to a biological environment including but not limited to sugars, amino acids, peptides, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state, emotional state, or social behaviors. The presence, absence, reduction, upregulation of the biomarker is associated with and is indicative of a particular state.

The term "aptamer-based sensor" as used herein refers to a sensor on which the binding of a target may emit a signal detectable through spectroscopic detection techniques such as SERRS, SERS or SEF (herein collectively Surface Enhanced Spectroscopy). The term "Surface Enhanced Spectroscopy" as used herein indicates signal enhancement techniques where signal detection from corresponding spectroscopic probes is performed in connection with a metal surface. Exemplary spectroscopic techniques suitable to detect aptamer based sensor herein described comprise including Surface-Enhanced Resonance Raman Spectroscopy (SERRS), Surface-Enhanced Raman Spectroscopy (SERS), Surface-Enhanced Fluorescence (SEF), Surface-Enhanced Infrared Absorption (SEIRA), Surface-Enhanced Hyper-Raman Scattering (SEHRS), Surface-Enhanced Coherent Anti-Stokes Raman Scattering (SECARS), and additional techniques identifiable by a skilled person.

The term "chromatography" as used herein refers to a process in which a chemical mixture carried by a liquid or gas is separated into components as a result of differential distribution of the chemical entities as they flow around or over a stationary liquid or solid phase.

The term "liquid chromatography" or "LC" as used herein means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

The term "high performance liquid chromatography" or "HPLC" (sometimes known as "high pressure liquid chromatography") as used herein refers to liquid chromatography in which the degree of separation is increased by forcing the mobile phase under pressure through a stationary phase, typically a densely packed column.

The term "turbulent flow liquid chromatography" or "TFLC" (sometimes known as high turbulence liquid chromatography or high throughput liquid chromatography) as used herein refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., J Chromatogr A 854: 23-35 (1999); see also, U.S. Pat. Nos. 5,968,367, 5,919,368, 5,795,469, and 5,772,874, which further explain TFLC. When a fluid is flowing turbulently, it flows in eddies and whirls (or vortices), with more "drag" than when the flow is laminar. Many references are available for assisting in determining when fluid flow is laminar or turbulent (e.g., Turbulent Flow Analysis: Measurement and Prediction, P. S. Bernard & J. M. Wallace, John Wiley & Sons, Inc., (2000); An Introduction to Turbulent Flow, Jean Mathieu & Julian Scott, Cambridge University Press (2001)).

The term "gas chromatography" or "GC" as used herein refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

The term "mass spectrometry" or "MS" as used herein refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

The term "survey-based data" and "survey database" as used herein refers to data that is collected actively by obtaining answers to questions from an individual, selected from a database query or passively by accumulation of data via incorporation of data due to association with an individual or group of individual's activities or experiences collected, for example via inputs from devices such as a phone or sensor that collects information from temporal and/or location based associations or databases harboring information based on a personal experiences, genetics, biological molecules, preferences, desires, personality traits, habits, wellness, emotional states or other characteristics. The answers to the questions, and, optionally, the circumstances under which the survey is conducted, may comprise survey-based data. The circumstances under which the survey is conducted may include the identity of the individual being or group of individuals or non-human individuals surveyed, the time, location, or any other event related to the survey. The data may be collected through various online forums or media, such as Facebook or survey panels.

The term "classification" as used herein refers to an algorithm of predicting the number of sets to which an item belongs by building a model based on some predictor variables. A "classification tree" is a decision tree that places categorical variables into classes.

The term "clustering algorithm" as used herein refers to an algorithm for finding groups of items that are similar. It divides a data set so that records with similar content are in the same group, and groups are as different as possible from each other. When the categories are unspecified, this is sometimes referred to as unsupervised clustering. When the categories are specified a priori, this is sometimes referred to as supervised clustering.

The term "discriminant analysis" as used herein refers to a statistical method based on maximum likelihood for determining boundaries that separate the data into categories.

The term "k-nearest neighbor" as used herein refers to a classification method that classifies a point by calculating the distances between the point and points in the training data set. Then it assigns the point to the class that is most common among its k-nearest neighbors (where k is an integer).

The term "machine learning" as used herein refers to a computer algorithm used to extract useful information from a database by building probabilistic models in an automated way.

The term "regression tree" as used herein refers to a decision tree that predicts values of continuous variables.

The term "supervised learning" as used herein refers to a data analysis using a well-defined (known) dependent variable. All regression and classification algorithms are supervised. In contrast, "unsupervised learning" refers to the collection of algorithms where groupings of the data are defined without the use of a dependent variable. The term "test data" refers to a data set independent of the training data set, used to evaluate the estimates of the model parameters (i.e., weights).

The term "promotion" or "offer" as used herein means providing any type of information in any language or translated into any language or scripting social media content in any language or translated into any language relating to any product or service for the purpose of promoting that product or service, and includes, but is not limited to, any type of advertisement, advertising, marketing, coupon, discount, offer, daily deal, auction used for promotion or offer, and the like.

The term "product" as used herein refers to any product described herein, or as known in the art: non-limiting examples of products include, but are not limited to: merchandise, retail products, wholesale products, virtual products, electronics, clothing, food, water, beverages, commercial products, household or housing products, cleaning products, footwear, appliances, autos, trucks, motorcycles, boats, airplanes, commercial and residential construction products, music, audio, and video products, books, computers, hardware, systems, operating systems, software, products relating to mobile banking and mobile wallet services, products relating to entertainment or shopping, products relating to penny auctions or online auctions, products relating to affiliate services, products relating to e-commerce, products relating to sports, media, musical instruments, educational products, financial products, travel & hospitality products, real estate products, sports and sporting events, information on market trends and predictions, mortgage quotes, loans, insurance, advertising, messaging, news feeds, weather, news, real estate products (e.g. vacant land, residential, commercial, recreational, retail, shopping malls, hotels, motels, golf courses, casinos, resorts, marinas, industrial, vacation, time shares, condominiums, multifamily, and other types of real estate, etc.), relocation products, internet marketing, home improvements/remodeling (home warranties, insurance, indoor and outdoor furniture, fixtures, windows, siding, roofing, heating/cooling, solar, plumbing, electrical, mechanical, and similar products), grocery, livestock, hair products, resorts, floor coverings, furniture, fixtures, gaming products, personal products, beauty care products, weight loss products, skin care products, dietary products, dietary supplements, sports supplements, nutrients, vitamins and the like.

The term "product provider" as used herein refers to any provider (in any form, e.g., but not limited to a discoverer, inventor, developer, manufacturer, co-developer, marketer, distributor, wholesaler, retailer, importer, exporter, seller, reseller, auctioneer, bidder, agent, representative, and the like) of any product, including a consumer product.

The term "service" as used herein refers to any service described herein, or as known in the art: non-limiting examples of services include, but are not limited to: search engines or search requests; social, local, mobile search, mobile services, mobile banking and mobile wallet services, entertainment, shopping, penny auctions or online auctions, affiliate services, e-commerce, sports, media and entertainment, educational, personal & financial services, travel & hospitality services, real estate, sports and sporting events, services by service providers, online dating, online gambling, gaming, retail stores, virtual communities, real estate services, advertising, messaging, news feeds, weather, news, real estate services (e.g. leasing, buying or selling of vacant land, residential, commercial, recreational, retail, shopping malls, hotels, motels, golf courses, casinos, resorts, marinas, industrial, vacation, time shares, condominiums, multifamily, and other types of real estate, etc.), brokers, agents, relocation services, internet marketing, concierge, transportation, lenders, appraisers, developers, contractors, inspectors, home improvements/remodeling (home warranties, insurance, roofing, heating/cooling, solar, plumbing, electrical, mechanical, and similar types of services), merchandizing, cleaning, transportation, banking, auctions, estate planning, husbandry, veterinary, medical, cosmetic, spa, moving, relocation, copying, office, management, filing, accountant, beverage services, and the like.

The term "service provider" as used herein refers to any provider (in any form, e.g., but not limited to a discoverer, inventor, developer, manufacturer, co-developer, marketer, distributor, wholesaler, retailer, importer, exporter, seller, reseller, auctioneer, bidder, agent, representative, physician and the like of any service.

The terms "undirected method" or "undirected analysis" as used herein refer to routine or repeated monitoring and/or collection of multiple biomarkers or other molecules recovered from a living organism in a combined exploratory, monitoring manner without necessarily having a pre-determined expectation of outcomes or results, particularly when estimating the effects of simultaneously occurring combinations of inputs, environments or conditions. Data related to behavior can also be collected or monitored in an undirected method.

The term "wellness" as used herein refers any actual or perceived improved state of being including emotional, health, fitness, psychological, beauty, confidence and desire as compared to a comparative state of being of a person. This is not the traditional model of health where wellness is determined merely by the absence of a disease or infirmity. Wellness in the context of the present invention is an improved state of functioning of an individual regardless of the individual's current health status or disability. Thus, wellness exists on a continuum and is unique to each individual person based on the individual's unique circumstances. Wellness may also be viewed as a holistic concept that looks at the individual as a whole and not just at the individual's blood pressure level or how much the individual weighs, or how well the individual manages stress.

The term "biosensor" as used herein refers to a sensor which converts an interaction between a target and a recognition molecule into a signal such as an electric signal, so as to measure or detect a target. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, aptamer/ligand, or hormone/receptor. The biosensor operates on the principle that a substance having an affinity with a receiving molecule, as described above, is immobilized on a substrate to be used as a molecule-recognizing substance, so that the corresponding substance can be selectively measured.

The term "behavior" as used herein includes lifestyle behavior, activities or actions that impact wellness, consumption activities, exercise, meditation, preferences, personality traits, and desires.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

The present invention provides a novel method of integrating behavioral and/or emotional phenotype such as social behavioral phenotype or social emotional phenotype with a biological phenotype. The invention also provides a database of such information for use by merchants, consumers and others. In the method and database of the present invention, a correlation is made between biological phenotypes and behavioral and/or emotional phenotypes. This may be seen as analogous to the traditional approach of correlating genotype to phenotype or genotype to genotype.

Biological phenotypes are determined by quantifiable genetic, developmental and environmental variables, which can be measured as biomolecular states, such as genome sequence, epigenomic modifications, RNA and microRNA levels, protein levels, protein folding and modifications, metabolite levels and electrical signals. A biological phenotype is the composite of an organism's observable characteristics or traits: such as its morphology, development, biochemical or physiological properties, phenology, behavior, and products of behavior (such as a bird's nest). Biological phenotypes result from the expression of an organism's genes as well as the influence of environmental factors and interactions between the two. In the methods of the present invention, biomolecular states are measured using genetic, developmental and/or environmental or other variables, such as those described herein.

Biological phenotype may comprise polypeptides presented in a sample. The polypeptide composition in the sample may be analyzed by any technology known to a person skilled in the art. For example, the polypeptides in the sample may be separated by a method selected from various chromatographic methods (such as LC, HPLC, TFLC, and GC), gel-electrophoresis-based methods (such as 2D-SDS gel electrophoresis), and exchange column-based technologies. The individually separated polypeptides may then be detected by, for example, protein immunostaining, protein immunoprecipitation, immunoelectrophoresis, immunoblotting, Western blot, spectrophotometry, mass spectrometry, sequencing, and enzymatic assays. More details on methods for analyzing polypeptides in a sample may be found, for example, in WO 00/11208, which discusses mass spectrometric methods for analysis of polypeptides; Cravatt and Sorenson, "Current Opinion in Chemical Biology," (2000) 4(6): 663-668, which discusses chemical strategies for analyzing polypeptide function; U.S. Pat. No. 4,433,051, which discusses α-difluoromethylornithine for use in polypeptide analysis; U.S. Pat. No. 6,127,134, which discusses difference gel electrophoresis using matched multiple dyes; Gygi et al., *Proc. Natl. Acad. Sci.* USA (2000) 97:9390-5, which discusses the use of 2D gel electrophoresis in conjunction with mass spectrometry to analyze yeast polypeptides; and Aebersold et al., PCT/US99/19415, which discusses digestion of labeled polypeptide samples.

Mass spectrometry analysis is particularly suitable for the present invention, particularly for the discovery of new and existing biomarkers associated with particular behavioral and/or emotional states, and for biomarker measurement.

Another technology that is particularly suitable for the present invention is a protein microarray. The protein microarray may be used to detect polypeptides in the sample on a large scale. The microarray-based technology also does not require a preliminary step of separating polypeptides from the sample. A protein microarray consists of a support surface such as a glass slide, nitrocellulose membrane, bead, or microtitre plate, to which an array of capture proteins is bound. The capture proteins, typically antibodies, bind to the target polypeptides in the sample. The polypeptides bound to an antibody on the microarray are then detected using a laser scanner. More details on protein microarrays can be found in U.S. Pat. Nos. 4,591,570; 4,829,010; 5,100,777, which are hereby incorporated by reference in their entirety.

Aptamers may be used to detect polypeptides in the sample. The aptamers for a specific a target polypeptide may be discovered by known methods. In one embodiment, nucleic acid ligands are discovered using an in vitro selection process referred to as SELEX (Systematic Evolution of Ligands by Exponential enrichment). See for example Gold et al. (U.S. Pat. Nos. 5,270,163 and 5,475,096), the contents of each of which are hereby incorporated by reference herein in their entirety. SELEX is an iterative process used to identify a nucleic acid ligand to a chosen molecular target from a large pool of nucleic acids. The process relies on standard molecular biological techniques, using multiple rounds of selection, partitioning, and amplification of nucleic acid ligands to resolve the nucleic acid ligands with the highest affinity for a target molecule. The SELEX method encompasses the identification of high-affinity nucleic acid ligands containing modified nucleotides.

In some embodiments, aptamers may be introduced into the sample to bind to target polypeptides, and thus form complexes of aptamer/polypeptide. The aptamers may be tagged, where the tag is for facilitating removal of unbound aptamers and other molecules in the sample from the complexes to remove potential sources of noise in the assay. Detecting the aptamer portion of the complexes will discover the bound polypeptides, which gives information on which polypeptides are in the sample. More details on this assay are described in US 2009/0042206, which is incorporated by reference herein in its entirety.

In some other embodiments, aptamers may be fixed on an array for detecting a large number of polypeptides in a single assay. Each aptamer is fixed at a microscopic spot on the surface of the array. The binding of a polypeptide to its specific aptamer on the array may be detected by direct fluorescence detection of fluorescent reporters, fluorescence anisotropy, FRET, SPR imaging, and electrochemical detection. See Baldrich, "Aptamer array", *Methods Mol Biol.*, volume 671, pages 35-54, 2011, which is incorporated hereby in its entirety.

Biosensors are also particularly useful in the methods of the present invention in the detection of biomarkers.

In one embodiment, the biosensor comprises a semiconducting nanoparticle ion-sensitive field-effect transistor (ISFET) for detecting immunoglobulin G (IgG) in a modified conventional enzyme-linked immunosorbent assay (ELISA). Indium oxide and silica nanoparticles are layer-by-layer self-assembled with the oppositely charged polyelectrolyte as the electrochemical transducer and antibody immobilization site, respectively. The indium oxide nanoparticle ISFETs generate electric signals in response to the concentration of target IgG. The sandwiched ELISA structure catalyzes the conversion of the acidic substrate into neutral substance with the aid of horseradish peroxidase.

The pH change in the sample solution is detected by nanoparticle ISFETs. See Lee et al., "An electric detection of immunoglobulin G in the enzyme-linked immunosorbent assay using an indium oxide nanoparticle ion-sensitive field-effect transistor," *J. Micromech. Microeng.*, volume 22, page 015009, 2012, which is hereby incorporated herein by reference in its entirety.

It is contemplated that an individual can deliver a sample, or the data from the assay of a sample to a location where it can be used in a correlation analysis. Initially, one or more polypeptides, and/or the entire proteome will be assayed. In a preferred embodiment, one protein is assayed, for example a hormone, for example adrenaline. In another embodiment, 5 proteins are assayed. In another embodiment 10 proteins are assayed. In another embodiment, 50 proteins are assayed. In another embodiment 100 proteins are assayed. In another embodiment, 500 proteins are assayed. In another embodiment 1000 proteins are assayed. In another embodiment, 2000 proteins are assayed. In another embodiment 2500 proteins are assayed. In another embodiment, 3000 proteins are assayed. In another embodiment up to 10,000 proteins are assayed.

The specific state of the proteome (the entire set of proteins expressed by a genome, cell, tissue or organism) in a given cell, tissue, or organism is known as the proteotype. The proteotype is the proteomic state that uniquely underlies a phenotype. Proteotyping mines the genetic information of a gene at the protein level by visualizing unique amino acid signatures. As a result, many protein forms resulting from a single gene can be visualized. The proteotype integrates constraints imposed by the genotype, the environment, and by developmental history (i.e., a skin cell has a different proteotype than a heart cell with the same genotype in the same environment). The proteotype can directly and partially determine biological phenotype since all molecules are made by and regulated by proteins. Thus, the biological proteotype can be used to directly infer genotype contributions to phenotype (because peptides map to DNA), and enables a synthetic reconstruction of phenotype (changes in protein levels or in post-translational modifications can be engineered). A complete description of the proteotype can partially define a biological phenotype at the molecular level.

Activities and actions of an organism are affected by proteins. As a result, proteins can be measured to demonstrate the biomolecular state of an individual. The large-scale study of proteins, "proteomics", is currently used to diagnose disease and to determine if a gene is expressed in a sample. In the past, less efficient methods were employed to determine protein related activities, for example nucleic acid (RNA) levels were measured. Proteomics can be more accurate for certain studies concerning protein related activity than determining, for example, RNA levels, since transcription rates, RNA half-life, protein half-life and protein distribution all impact whether a protein is available at a sufficient level to allow a protein related activity to occur.

While a nucleic acid contributes to protein levels by encoding a protein and thereby allowing a protein to be expressed, whether a protein is actually present and in sufficient quantity is determined by a myriad of factors. Thus, measuring proteins is a way to decrease error and reduce the potential for misinterpretation of correlations. In an embodiment of the present invention, proteomics and/or proteotyping is utilized to measure the biomolecular state of an individual, or the biological phenotype of an individual.

Proteins that are always present or always absent are predictive of future social behavior since their presence or absence correlates with a response to a query, as set forth herein. Further, proteins that are induced upon a response allow further genetic association, which allows DNA to be predictive (however, it is recognized that the gene that encodes the protein is not necessarily the gene inducing the particular protein level shift).

There are studies suggesting correlations between the proteotype of an individual and human behaviors. For example, Jagannath et al., "The CRTC1-SIK1 Pathway Regulates Entrainment of the Circadian Clock," *Cell*, volume 154, pages 1100-1111, 2013, found that the presence of certain proteins in the CRTC1-SIK1 pathway may change a mammal's reaction to natural light, i.e. altering circadian system functions. The authors analyzed the transcriptome of relevant cells responding to light-regulation and identified a key role for salt inducible kinase 1 (SIK1) and CREB-regulated transcription coactivator 1 (CRTC1) in altering circadian system functions.

Other examples include AMPK (AMP-Activated Protein Kinase) that is normally switched on during exercise, catecholamines such as adrenalin that are linked to stress and can be identified in urine tests common, epinephrine that is associated with focus and fight or flight reactions, dopamine that is associated with pleasure, with higher levels observed in extroverts, and IL6 that is associated with stress and depression.

The present invention takes a systematic approach to correlate biological phenotypes (including polypeptides) to behavioral and/or emotional phenotypes, particularly for humans.

Biological phenotype may be determined by polynucleotides present in the sample. Known methods for detection of polynucleotides may be used in the present invention. In some embodiments, several technologies may be used in combination: for example, sequencing based technologies, homogeny based technologies, and aptamer based technologies.

In sequencing based technologies, the polynucleotides in a sample may be separated by electrophoresis and each species of the polynucleotides in the sample may be sequenced by conventional polynucleotide sequencing technologies. These technologies are widely described in the literature, for example, Pettersson et al., "Generations of sequencing technologies," *Genomics*, volume 93, pages 105-111, 2009.

For sequencing mRNAs in the sample, due to the tendency of mRNA to degrade, it may be desirable to copy mRNAs to cDNAs before carrying out sequencing. Because DNA is generally much more stable than RNA, converting mRNA to cDNA will allow the samples to be stored and sequenced later.

Homogeny based technologies, they are based on the principle that a polynucleotide in the sample will hybridize with a nucleic acid probe that is complementary to or matches with the polynucleotide. In some embodiments, the nucleic acid probe is an oligonucleotide or oligonucleotide analog that is conjugated to labels, which are usually fluorescent chemical compounds such as fluorophores. Suitable oligonucleotide analogs include but are not limited to oligonucleotides containing at least one residue of locked nucleic acid or peptide nucleic acid. Preferably, the homogeneous detection is based on competitive hybridization (EP0232967B1, incorporated hereby in its entirety) or on a probe that is labeled with two labels, one of which is capable of absorbing or quenching the signal emitted by the other label when the probe is not hybridized to a target sequence.

Examples of such probes have been described in e.g. in U.S. Pat. Nos. 5,925,517; 6,103,476; and 6,150,097, as well as EP 0 792 374 B1, which are incorporated by reference in their entirety.

In some embodiments, the homogeny based method employs oligonucleotide microarrays, or DNA microarrays. In the DNA microarray technology, the oligonucleotide probes are fixed on at a microscopic spot on a solid surface. Thus, tens of thousands of probes may be fixed on a single chip, which enables parallel detection of up to thousands of polynucleotides in a sample. The DNA microarray may be custom built to specifically detect certain species of polynucleotides in a sample. In some embodiments, commercial DNA microarrays may be used for detecting as many polynucleotides as possible in a sample. Commercial DNA microarray include these made by Affymetrix "Gene Chip", Illumina "Bead Chip", Agilent single-channel arrays, the Applied Microarrays "CodeLink" arrays, and the Eppendorf "DualChip & Silverquant." More details on the DNA microarray technology may be found in Shalon D, Smith S J, Brown P O (1996). "A DNA microarray system for analyzing complex DNA samples using two-color fluorescent probe hybridization". *Genome Res* 6 (7): 639-645; Yuk Fai Leung and Duccio Cavalieri, Fundamentals of cDNA microarray data analysis. TRENDS in Genetics Vol. 19 No. 11 November 2003; Schena M, Shalon D, Davis R W, Brown P O (1995). "Quantitative monitoring of gene expression patterns with a complementary DNA microarray". *Science* 270 (5235): 467-470; Pease A C, Solas D, Sullivan E J, Cronin M T, Holmes C P, Fodor S P. (1994). "Light-generated oligonucleotide arrays for rapid DNA sequence analysis". *PNAS* 91 (11): 5022-5026, which are hereby incorporated by reference in their entirety.

In some embodiments, aptamers specifically binding to polynucleotides may be used for detecting polynucleotides in the sample. The aptamers for specific target polynucleotides may be discovered by any method known in the art, such as the SELEX method discussed above. In some embodiments, the aptamers are introduced into the sample to bind to target polynucleotides, thus forming complexes. The aptamers may be tagged, where the tag may be used for facilitating removal of unbound aptamers and other molecules in the sample from the complexes. Finally, detecting the aptamer portion of the complexes will discover the bound polynucleotides, which gives information on which polynucleotides are in the sample. More details on this assay are found in US 2009/0042206.

In some other embodiments, the aptamers may be fixed on an array for detecting a large number of polynucleotides in the sample. Each aptamer is fixed at a micro-spot on the surface of the array. The binding of a polynucelotide to its specific aptamer on the array may be detected by direct fluorescence detection of fluorescent reporters, fluorescence anisotropy, FRET, SPR imaging, and electrochemical detection. See Baldrich, "Aptamer array", *Methods Mol. Biol.*, volume 671, pages 35-54, 2011.

In some embodiments, the polynucleotides in the sample may be amplified before being detected. A typical technology for amplifying polynucleotides is the polymerase chain reaction (PCR), as described in Saiki et al., "Enzymatic amplification of beta-globin genomic sequences and restriction site analysis for diagnosis of sickle cell anemia," 1985 Science 230, 1350-1354, which is hereby incorporated by reference in its entirety. With PCR, it is possible to amplify a single copy of a specific polynucleotide sequence to a level that can be detected by several different methodologies (e.g., staining, hybridization with a labeled probe, and incorporation of biotinylated primers followed by avidin-enzyme conjugate detection, incorporation of 32P-labeled deoxynucleotide triphosphates, such as dCTP or dATP, into the amplified segment).

This PCR based technology may be modified to achieve high specificity. For example, nested PCR may be used in some embodiments of the present invention. For RNA molecules in the sample, reverse transcription PCR may be used to amplify the RNA molecules to DNA molecules.

There are isolated studies suggesting correlations between genetic variations of an individual and human behavior. For example, Ebstein et al., "Genetics of human social behavior," *Neuron*, volume 65, pages 831-844, 2010 discloses that, based on twin and family studies, human characteristics such as empathy, altruism, sense of equity, love, trust, music, economic behavior, and even politics are at least partially determined by genes. Genes such as the arginine vasopressin receptor and the oxytocin receptor contribute to social behavior in a broad range of species from voles to man. Other polymorphic genes such as those encoding for dopamine reward pathways, serotonergic emotional regulation, or sex hormones are also found to correlate with elaborate social behaviors. Any one or more of these correlations may be employed in a database of the present invention.

Biological phenotype may also be determined by metabolites in the sample. Metabolites may be macromolecules or small chemicals produced by chemical reactions in the body. Some common metabolites include amino acids, peptides, nucleotides and nucleosides. The metabolites are usually present in solution (e.g. bodily fluids). However, metabolites may also be in present in a gas, such as in breath and fart gas.

In some embodiments, there may be two steps required for detecting metabolites in the sample: separating the metabolites from the sample and then identifying the separated metabolites. The technologies for separating metabolites from the sample include the same ones as described above for separating polypeptides, such as chromatographic technologies and electrophoresis-based technologies. In some embodiments, gas chromatography offers a very high resolution, but may require chemical derivatization for many biomolecules. This technology is especially suitable for analyzing large and/or polar metabolites.

In some other embodiments, high performance liquid chromatography offers the advantage of being able to separate a very wide range of metabolites, though it typically has low resolution. In some other embodiments, capillary electrophoresis may be used to separate metabolites from the sample. Capillary electrophoresis offers the advantage of high separation efficiency and is suitable for use with a wider range of metabolite classes. Other methods for separating metabolites include "liquid chromatography" including reverse phase liquid chromatography (RPLC), high performance liquid chromatography (HPLC), and turbulent flow liquid chromatography (TFLC), sometimes known as high turbulence liquid chromatography (HTLC) or high throughput liquid chromatography.

The individually separated metabolites may then be identified using technologies such as mass spectrometry, which is both sensitive and specific. For example, Nanostructure-Initiator mass spectrometry, a desorption/ionization approach that does not require the application of matrix and thereby facilitates metabolite identification, may be used as described in Northen T. R, et al., "Clathrate nanostructures for mass spectrometry," *Nature* 449 (7165): 1033-1036 (October 2007). Secondary ion mass spectrometry, which uses a high-energy primary ion beam to desorb and generate secondary ions from a surface, can also be employed. The primary advantage of secondary ion mass spectrometry is its high spatial resolution (as small as 50 nm). However, secondary ion mass spectrometry has limited sensitivity to metabolites with a molecular weight >500 Da.

In some embodiments, nuclear magnetic resonance spectroscopy (NMR) may be employed to identify metabolites. NMR has the advantage that it does not require separation of the metabolites from the sample. All of the metabolites in the sample may be measured simultaneously and concentrations of metabolites may also be determined. Suitable NMR methods can be found in Griffin J. L., "Metabonomics: NMR spectroscopy and pattern recognition analysis of body fluids and tissues for characterisation of xenobiotic toxicity and disease diagnosis," *Curr. Opin. Chem. Biol.*, 7 (5): 648-654, 2003.

Metabolites may be present in blood, urine, sweat, breath, stool, and farting gas. For example, by one estimate, there may be over 3,000 compounds in human urine (Bouatra et al., "The human urine metabolome," *PLoS ONE*, volume 8, page e73076, (2013). The study used different metabolite analytical platforms including NMR, GC-MS, DFI/LC-MS/MS, ICP-MS and HPLC. The authors built a database on urine metabolites that contains 2651 confirmed human urine metabolite species, their structures (3079 in total) and concentrations. The database is accessible at http://www.urinemetabolome.ca. Each of these urine metabolites can be used in the present invention either alone or in combination with other urine metabolites.

Antibodies and aptamers that can specifically bind to metabolites can be used to detect metabolites in the sample, in a fashion that is similar to using antibodies and aptamers to detect polypeptides and polynucleotides in the sample, as discussed above.

There are studies suggesting that metabolites in a bodily fluid of an individual can be correlated with human behaviors. For example, Kandel et al., "Urine nicotine metabolites and smoking behavior in a multiracial/multiethnic national sample of young adults," *Am. J. Epidemiol.*, volume 165, pages 901-910, (2007) indicates that urine metabolites generated from nicotine metabolism can be correlated with human smoking behavior. Specifically, the ratio of trans-3'-hydroxycotinine to cotinine in urine can be correlated with multiple measures of smoking behavior and nicotine dependence. This finding is consistent with those from laboratory studies of older smokers based on intravenous infusion of nicotine.

Another example is from Träskman et al., "Monoamine metabolites in CSF and suicidal behavior," *Arch. Gen. Psychiatry*, volume 38, pages 631-636, (1981) indicating that several monoamine metabolites in the cerebrospinal fluid can be correlated with suicidal behaviors. These metabolites include 5-hydroxyindoleacetic acid (5-HIAA), homovanillic acid (HVA), and 3-methoxy-4-hydroxyphenyl glycol (MHPG). Humans that made suicide attempts have a significantly lower 5-HIAA level than the controls, especially those who had made more violent attempts. Concentrations of 5-HIAA were also lower than normal in suicidal patients who were not diagnosed as depressed at the time of lumbar puncture, while HVA levels were lowered only in the depressives. A similar observation was also made in urine (Ostroff et al., "The norepinephrine-to-epinephrine ratio in patients with a history of suicide attempts," *Am. J. Psychiatry*, volume 142, pages 224-227, (1985)), where three depressed patients who had made serious suicide attempts exhibited a significantly lower 24 hour urine norepinephrine to epinephrine (EPI) ratio than 19 depressed patients who had made no suicide attempts.

Each of the above-described correlations can be implemented in the present invention, as well as various combinations of the correlations. In addition, other correlations not mentioned herein can be employed in the present invention to build a database that can be used by various parties that may find such correlations useful.

Biological phenotype may also be determined from microbes present in the sample. Microbes are live organisms containing specific polypeptides and polynucleotides. One way to detect microbes is by detecting a biomolecule that is specific to a microbe. The biomolecule may be a genomic DNA (for microbes with a DNA genome), a genomic RNA (for microbes with a RNA genome such as RNA viruses), or a microbial RNA such as mRNA. Therefore, the methods for detecting polynucleotides as described herein may also be used to detect microbes in the sample.

Microbes may also be detected from specific polypeptides that are produced by the microbes. Therefore, the methods for detecting polypeptides described herein may also be used to detect microbes in the sample. If the specific polypeptides are present inside the microbes, the microbes may need to be lysed to release the specific polypeptides for detection.

Conventional culturing may also be used to detect microbes in the sample. Microbes may grow on a culture and can be detected and identified by their morphology (observed by microscopy) or surface marker molecules (which may be detected by, for example, an antibody).

Some bacteria in humans have been found to alter human behaviors. In a scientific news article, "Gut feelings: the future of psychiatry may be inside your stomach," available at http://www.theverge.com/2013/8/12/4595712/gut-feelings-the-future-of-psychiatry-may-be-inside-your-stomach, it was disclosed that multiple studies found that alteration of the bacteria population in the guts of mice will significantly change the behavior of the mice. In addition, the news article also mentioned that doctors have been using probiotics to change the microbial populations in human guts in order to manage obsessive-compulsive disorder and Attention Deficit Hyperactivity Disorder (ADHD). Probiotics are known to add bacteria to or balance the microbial population (microflora) in human guts.

Bacteria in humans are also found capable of affecting the human tendency towards obesity (Greenfieldborce, "Fat Bacteria in Human Guts Tied to Obesity," available at http://www.npr.org/templates/story/story.php?storyId=6654607. It is indicated that obese mice have significantly different bacteria in their guts, in comparison with skinny mice.

It is believed that the microbes in human body actively interact with their human hosts. One survival strategy of microbes is manipulating host cell fate and orchestrating inflammatory responses. Microbes may specifically affect many host signaling pathways and host cell gene expression through a number of known mechanisms, thereby influencing human behavior and emotions.

The microbes in human guts will be found in stool and therefore may be easily detected. The number of microbial species in human guts is very large. By one estimate, there may be over 320,000 viruses in mammals (see "First estimate of total virus in mammals," available at http://phys.org/print297403030.html).

Biological phenotype may also be determined by inorganic compounds or ions in the sample. For example, the pH of the sample is actually the concentration of $H^+$ in the sample. $K^+$, $Na^+$, $Mg^{2+}$, $Ca^{2+}$, $Mg^{2+}$, $Cl^-$, $HCO_3^-$, $PO_4^{3-}$ and $OH^-$ may also be detected and quantified. Examples of suitable assays are described in Wan et al., "Determination of major inorganic ions in blood serum and urine by capillary electrophoresis with contactless conductivity detection," *Analytica Chimica Acta*, volume 525, pages 11-16, 2004; US 2003/0045827; and Xia et al., "Colorimetric detection of DNA, small molecules, proteins, and ions using unmodified gold nanoparticles and conjugated polyelectrolytes," *PNAS*, vol. 107, pages 10837-10841, 2010, which are hereby incorporated by reference in their entirety. In addition, assays known to a person skilled in the art that are capable of detecting inorganic compounds or ions in the samples may be used in the present invention.

The foregoing represent examples of the types of data that can be collected as well as methods to collect and analyze samples for use in the present invention.

In the present invention, data can be collected in an undirected method. Measurements of unknown states can be made, and multiple biomarkers and/or behaviors or emotional states can be measured simultaneously. Measurements can be taken using non-invasive methods. Longitudinal measurements can be taken, enabling detection for warning and guidance versus detection for specific diagnosis.

In some embodiments, the present invention may also collect map location data on where the biological phenotype data is measured. This may be based on a mobile device that has an installed map service such as Google maps, Yahoo maps, and Mapquest. In addition, this mobile device may also have a function of monitoring environmental factors at the location where the biological phenotype data is measured. These environmental factors may include weather (temperature, humidity, sunny/raining), UV light intensity, pollen count, etc.

In a preferred embodiment of the present invention, data collected includes data from location (map) which can optionally be correlated with time at the location and any orthogonal data from the location such as, but not limited to, temperature, altitude noise, altitude, wind, humidity, pollution, oxygen, sunshine, pollen, crowd density, concrete, grass, night, day, near highway and traffic density at that time, aircraft flying, cosmic radiation levels, radon exposure, clothing and physiological conditions. Thus, in this embodiment, other data is collected and saved in addition to measurement of one or more biomarkers so that such other data can be correlated with or used on conjunction with the biomarker data to predict one or more human behaviors and/or emotional states.

It is further recognized that other biological molecules, such as peptides, proteins, metabolites, hormones and small molecules, affect and/or indicate activities and behavior of an organism. For example, the female reproductive hormone oxytocin has been correlated to generous and caring behavior. Quantitative physical biological component inputs of the present invention can include measurement or description of DNA type, RNA levels, microRNA types or levels, protein levels, proteotype, metabolic levels or even qualitative or quantitative MRI. In another embodiment of the present invention, measurement of biological molecules, such as peptides, hormones and/or small molecules, or any combination thereof, is performed to measure the biomolecular state of an individual.

To be more effectively detect/analyze the biological phenotype of a human, computer chips can be utilized to directly analyze, or present samples to a device (for example, a computer) that will analyze the sample. For example, nanotechnology has been used to create devices for testing disease states. Body gases have been measured on a device using carbon nanotube sensor technology to diagnose disease. For example, nucleic acids are immobilized on a detection chip, individuals expose the chips to body gas(es), nucleic acids bind variably to nucleic acid sequences on the chip resulting in unique patterns after detection, and the presence or absence of a gas is correlated to disease. Proteins have also been coupled with carbon nanotube transistors, and the resulting devices transduce signals associated with protein binding events, providing a general method for the study of protein function using an electronic readout in a nanotube format. These represent examples of methods to collect and analyze samples for use in the present invention.

The behavioral and/or emotional phenotype of the same person from whom the sample is collected may also be determined by surveying the person or a third party that has observed the person. There are different ways to determine the behavioral and/or emotional phenotype of an individual, such as third party observation and self-evaluation by answering questions on social behavior and emotions. In some embodiments, a questionnaire may be used to assessing the behavioral and emotional states of the person. In some embodiments, both third party observation and a self-completed questionnaire may be used to determine the behavioral and/or emotional phenotype of the person. Data may be collected through various online forums or media.

In some embodiments, individuals, or individuals knowledgeable about another individual's social behavior/emotions, will complete a behavioral questionnaire or series of questions designed to indicate or evaluate feeling, actions, preferences, mood, sensation, senses, or other physical, biological, emotional, psychological, or mental states. For example, questions can be "Do you like riding motorcycles?", "Do you get nauseated on roller coasters?", "Are you married?", "Are you happy?", "Are you a republican?", "which texture do you prefer (show a picture)?", "do you prefer a hot climate or a cool climate?", "do you prefer the color red or the color yellow?", "Do you like to drive fast?" and/or other such questions whereby answers indicate individual preferences, feelings, behavior or other states. Information can be gathered about likes and dislikes in the form of visual presentations as well. For example, pictures can be shown to individuals and comments given by the individual regarding opinion, such as "I see it and I like it", "I see it and I don't like it, "I haven't seen it, but I will like it, "I haven't seen it, but I won't like it".

Emotional states include, but are not limited to, basic emotions such as feeling tenderness, or being excited, happy, sad, angry or scared. A person skilled in the art can design a questionnaire suitable for a specific situation in order to understand a particular aspect of human behavior and/or emotions.

The present invention contemplates that the biological phenotype of a person is not fixed or constant. The biological phenotype will change over time and can track the human's social behavioral and emotional changes over time.

Thus, in the method of the present invention answers from the behavioral and/or emotional questionnaire, or series of behavior questions, i.e., social behavioral/emotional phenotype, are then correlated with the biological phenotype. There are many algorithms that may be used to establish the correlation between biological phenotype and behavioral and/or emotional phenotype. In some embodiments, the correlation may be established using classification algorithms, such as clustering algorithms, which find rules that partition the data (biological phenotype and behavioral and/or emotional phenotype) into finite, disjoint, and previously known (or unknown) classes. In other embodiments, the correlation may be established using association algorithms, e.g., of summarization algorithms, which find the set of most commonly occurring groupings of items.

In some embodiments, an algorithm that may be used in the method of the present invention is s process of data classification for finding correlations between biological phenotype and behavioral/emotional phenotype. Classification is the process of finding common properties among a set of "objects" in a data set, and grouping them into various classes based on a classification scheme. Classification models are first trained on a training data set which is representative of the real data set. The training data is used to evolve classification rules for each class such that they best capture the features and traits of each class. Rules evolved on the training data are applied to the main database and data is partitioned into classes based on the rules. Classification rules can be modified as new data is added.

In another embodiment, the present invention uses a data mining algorithm based on association rules algorithms. The data mining task for association rules can be broken into two steps. The first step consists of finding all large item sets. The second step consists of forming implication rules with a user specified confidence among the large item sets found in the first step. For example, from a dataset on biological phenotype, one may find that an association rule such as a behavioral or emotional response is caused by (can be correlated with) a certain biological phenotype. Association rules can also be more complex, requiring that two or more criteria are met in order for the rule to be invoked.

Yet another data mining algorithm that may be used in the present invention is sequential pattern mining. This algorithm can be used to find sequential patterns which occur a significant number of times in the database. This analysis can be used to detect temporal patterns. Time-Series clustering is another data mining algorithm that can be used to detect similarities in different time series.

In yet another embodiment, the present invention uses a clustering algorithm for finding correlations between biological phenotype and behavioral and/or emotional phenotype. In general, clustering algorithms can be broadly classified into partitional and hierarchical clustering algorithms.

Partitional clustering attempts to determine k partitions that optimize a certain criterion function. The square-error criterion is a good measure of the within-cluster variation across all the partitions. The objective is to find k partitions that minimize the square-error. Thus, square-error clustering tries to make the k clusters as compact and separated as possible, and works well when clusters are compact clouds that are rather well separated from one another.

Hierarchical clustering is a sequence of partitions in which each partition is nested into the next partition in the sequence. An agglomerative method for hierarchical clustering starts with the disjoint set of clusters, which places each input data point in an individual cluster. Pairs of clusters are then successively merged until the number of clusters reduces to k. At each step, the pair of clusters merged are the ones between which the distance is the minimum. There are several measures used to determine distances between clusters. For example, pairs of clusters whose centroids or means are the closest are merged in a method using the mean as the distance measure ($d_{mean}$). This method is referred to as the centroid approach. In a method utilizing the minimum distance as the distance measure, the pair of clusters that are merged are the ones containing the closest pair of points ($d_{min}$). This method is referred to as the all-points approach.

In another embodiment, the present invention utilizes the hierarchical clustering Serial Linkage Method. This is an unsupervised clustering method in the same sense as K-means and fuzzy clustering. Here individual points are joined to each other by being close to each other in the input space. As these points are joined together, they define clusters. As the algorithm continues, the clusters are joined together to form larger clusters. Compared to K-means and fuzzy clustering, hierarchical clustering has the advantage that clusters can have arbitrary non-predefined shapes and the result correctly shows "clusters of clusters."

In still other embodiments, the present invention utilizes K-means and fuzzy clustering. Gaussian mixture models are a common version of this. These algorithms are "unsupervised" clustering methods. They assume the user has no outputs, but would like to group the data anyway according to inputs that are similar to each other. The idea is to choose a model for each cluster. For example, each cluster may consist of points inside a hyper-sphere centered at some location in the input space. These methods automatically determine the number of clusters, place them in the correct places, and determine which points belong to which clusters. An advantage to these algorithms is that they can be efficient algorithms and can do a good job of finding clusters.

In yet another embodiment, the present invention utilizes a Kohonen self-organizing maps (SOM) clustering algorithm. These algorithms are related to neural nets in the sense that gradient descent is used to tune a large number of parameters. The advantages and disadvantages are similar to those of neural networks. In relation to neural networks, Kohonen SOM clustering algorithms have the advantage that parameters can be more easily interpreted, though such algorithms may not scale up to high dimensions as well as neural nets can.

In another embodiment, the present invention uses Principal Component Analysis (PCA) for finding correlations between biological phenotype and behavioral and/or emotional phenotype. This is not a classification method per se. The purpose of PCA is to represent variation in a data set into a more manageable form by recognizing classes or groups. The assumption in PCA is that the input has a large number of dimensions (tens or even thousands of variables). PCA extracts a smaller number of variables that cover most of the variability in the input variables. As an example, suppose there are data along a line in 3-space. Normally one would use 3 variables to specify the coordinates of each data point. In fact, just 1 variable is needed: the position of the data point along the line that all the data lies on. PCA is a method for finding these reductions. An advantage to PCA is that it can be a reasonably efficient method whose reduction is well founded in terms of maximizing the amount of data variability explained with use of a smaller number of variables.

Principal component analysis (PCA) involves a mathematical procedure that transforms a number of (possibly) correlated variables into a (smaller) number of uncorrelated variables called principal components. The first principal component accounts for as much of the variability in the data as possible, and each successive component accounts for as much of the remaining variability as possible. Traditionally, principal component analysis is performed on a square symmetric matrix of type SSCP (pure sums of squares and cross products), Covariance (scaled sums of squares and cross products), or, Correlation (sums of squares and cross products from standardized data). The analysis results for matrices of type SSCP and Covariance do not differ. A Correlation object is preferably used if the variances of individual variates differ much, or the units of measurement of the individual data points differ, such as is the case when the analysis comprises data from behavioral, neurological, biochemical and physiological measures. The result of a principal component analysis on such objects will be a new object of type PCA.

In still another embodiment, the present invention uses a neural net or neural network algorithm for finding correlations between biological phenotype and behavioral and/or emotional phenotype. Such algorithms may use gradient descent on the number of classification errors made, i.e. a routine is implemented such that the number of errors made decreases monotonically with the number of iterations. Gradient descent is used to adjust the parameters such that they classify better. An advantage to neural nets is that such algorithms can handle high dimensional, non-linear, noisy data well.

The neural net can be trained with "supervision", i.e., a mechanism by which the net is given feedback by classifying its responses as "correct" or "incorrect". It eventually hones in on the correct output for each given input, at least with some probability. Such machine learning algorithms may be advantageously employed for either or both of vision classification components or data mining components of the instant invention.

Supervised learning requires the buildup of a library of readily classified data sets for input into the neural net. Although more economic in terms of the amount of data needed, supervised learning implies that only pre-determined classes can be ascribed to unseen data.

In certain embodiments, the method of the present invention may combine both types of learning for finding correlations between biological phenotype and behavioral and/or emotional phenotype: a supervised learning of the neural net until it correctly classifies a basic training set. Then an unsupervised learning to further subdivide the trained classes into meaningful sub-classes, or to add completely new sub-classes.

In yet another embodiment, the present invention utilizes a nearest neighbor algorithm for finding correlations between biological phenotype and behavioral and/or emotional phenotype. This is a true supervised learning method. There is a set of training data (inputs, i.e. data points, and outputs, i.e. classes) that are given in advance and just stored. When a new query arrives, the training data is searched to find the single data point whose inputs are nearest to the query inputs. Then the output for that training data point is reported as the predicted output for the query. To reduce sensitivity to noise, it is common to use "k" nearest neighbors and take a vote from all their outputs in order to make the prediction.

In yet another embodiment, the present invention uses a logistic regression algorithm for finding correlations between biological phenotype and behavioral and/or emotional phenotype. This is related to linear regression (fitting a line to data), except that the output is a class rather than a continuous variable. An advantage is that is method provides a statistically principled approach that handles noise well.

In still another embodiment, the present invention utilizes a Support Vector Machine algorithm for finding correlations between biological phenotype and behavioral and/or emotional phenotype. This also has a linear separator between classes, but explicitly searches for the linear separator that creates the most space between the classes. Such algorithms work well in many dimensions. Yet another embodiment relies on a Bayes Classifier algorithm. The simplest form is a naive Bayes classifier. These algorithms build a probabilistic model of the data from each class. Unsupervised methods above may be used to do so. Then, based on a query, the model for each class is used to calculate the probability that that class would generate the query data. Based on those responses, the most likely class is chosen.

The method of present invention uses one or more of the algorithms describe above to establish a relationship between certain biological measures (biological phenotype) and a behavioral and or an emotional response (behavioral and/or emotional phenotype).

In some embodiments, the present invention may also determine and use a physiological phenotype of the individual, along with biological phenotype, to establish a correlation with a behavioral and/or emotional phenotype. The physiological phenotype may include physiological parameters such as:

Physical—motion, anthropometrics (e.g. waist, height and weight measurements), tissue structure and/or composition.

Metabolic—vital signs (heart rate, blood pressure, respiration rate, temperature), basal metabolic rate and/or hydration status.

Cardiovascular/Pulmonary—heart functionality (ECG, heart rate variability), respiratory rate/volume, arterial resistance/stiffening, arterial blockage, venous return, peripheral circulation and/or microcapillary proliferation/circulation.

Organs—size, composition and functionality, (e.g. kidney functionality, liver functionality, adipose tissue disposition, skin thickness/plasticity), pupil dilation and/or galvanic response.

Muscular/Skeletal—electromuscular activity (e.g. latent or stimulated), strength, composition, oxygenation and/or density.

Gastro-Intestinal—digestive activity and efficiency.

The measurement of these physiological parameters is routine in the medical field and may be performed using known methods.

Thus, in some embodiments, the physiological parameters (physiological phenotype) of the person from whom the sample is collected may also be determined and used to establish a correlation between biological/physiological phenotype and behavioral and/or emotional phenotype.

In one embodiment, the present invention provides a method for correlating biological phenotypic data and behavioral and/or emotional phenotypic data, comprising: obtaining a sample comprising biological molecules from an individual, obtaining a survey on behavior and/or emotions from the individual; storing the behavioral and/or emotional phenotypic data in a survey database; analyzing the sample of biological molecules to determine the composition of biological molecules (biological phenotypic data); storing the biological composition data in a sample database; and correlating the data from the sample database to the data from the survey database.

The correlations between biological phenotypes and behavior and/or emotional phenotypes are for providing guidance to an individual for assisting the individual's daily living. The relationships may, among other goals, provide warnings to the individual for a risk of contracting a disease. Therefore, the present invention may provide guidance to the individual for mitigating the risk. In another embodiment, the relationship may suggest emotional states that may affect the individual's quality of life, such as a feeling of sadness, or emotional instability. The present invention may provide guidance to the individual for improving or correcting these emotional states.

The correlations of the present invention are not the same as diagnostics in the medical field, which are for identifying persons with a disease and the nature or cause of the disease, which may be based on measurement of a biomarker. One major difference is that diagnostics require a very low error rate and are regulated and monitored by the U.S. Food and Drug Administration, while the present invention aims at providing guidance to an individual for assisting the individual's daily living. Because the present invention does not provide medical treatments or therapies to the individual, it can potentially to tolerate a higher error rate than diagnostics.

Furthermore, diagnostics are typically based on a measurement of a biomarker that falls outside of a normal range. For example, the concentration of a biomarker in a sample may be abnormally low or abnormally high, which indicates the existence of a disease. On the other hand, the biological phenotype of the present invention is based on measurements of biomarkers in a range that may also include a normal range. Thus, the present invention provides guidance to an individual based on measurements that may be in one or both of normal and/or abnormal ranges.

In the method of the present invention, biological molecules, such as polypeptides, may be used as markers for emotional or behavioral phenotype of individuals. After and during collection of data, including data about the presence or absence of the biological molecule(s) and data from the behavioral or emotional state of the individual, the data may be integrated and analyzed. Data that is determined to correlate with the biological phenotypes (for example, bias data) is retained and data not correlating with biological phenotypes may be saved for future correlation analyses. The data is stored, and a database is created. Collection of data can continue, and best correlations can be ordered by rank with the best data retained and the lowest correlations optionally eliminated over time. The methods will reveal empirical correlations of biological molecules, or state, to a behavioral and/or emotional state.

In some embodiments, a ratio between two biomarkers may be used for a correlation with behavioral and/or emotional phenotypic data. In many situations, a ratio between two biomarkers may have a better correlation with the behavioral and/or emotional phenotypic data, in comparison with a single biomarker.

A ratio between a biomarker and a product of a housekeeping gene may also be used in some embodiments. Housekeeping genes are typically constitutive genes that are required for the maintenance of basic cellular functions, and are expressed in all cells of an organism under normal and patho-physiological conditions. Some housekeeping genes are expressed at relatively constant levels. Proteins expressed from these housekeeping genes, which are at a relatively constant level, can be used as an internal standard to which a biomarker is compared to and a ratio to the housekeeping gene product may be generated. More specifically, protein expression levels of housekeeping genes in a sample are determined and used to compare relative protein expression levels of biomarkers, thereby generating a ratio of biomarker to a housekeeping gene. Other constitutively expressed genes that are expressed at substantially constant levels can also be employed.

In these embodiments, the level of one or more biomarker relative to a housekeeping gene or other constitutively expressed gene in a sample may be determined, thus suggesting up regulation or down regulation of the biomarker in the sample. Up regulation and down regulation of biomarkers can reflect the biological condition in a way and with a precision not readily achieved by relying on biomarker or DNA sequencing alone. This ratio can be maintained over any degree of sample dilution, and therefore can be used with a wide range of assays having varying sensitivities. This ratio approach can be particularly effective when measuring biological molecules in settings such as a toilet or urinal, where volumes of urine will vary with respect to volumes of water.

In some embodiments, the present invention may include correlation of biomarkers to a placebo effect. In medicine, the placebo effect is a positive therapeutic effect claimed by a patient after receiving a placebo believed by the patient to be an active drug. The "placebo effect" as used herein is a beneficial or detrimental effect measured in the biomolecules in an individual following a particular treatment, event, or circumstance that arises from the individual's expectations or beliefs concerning the treatment, event or circumstance rather than from the treatment, event or circumstance itself. In an embodiment of the present invention, the correlations of the present invention include correlations of biological molecules to a placebo effect, based on co-occurrence of the biological molecule and the placebo effect. One example may be the presence of a biological molecule at the same time as, preceding or succeeding the placebo effect. Such biological molecules may be called "placebo effect biomarkers" because the biological molecule may be present with a placebo effect. These "placebo effect biomarkers" can be indicators of belief enhancement. These biomarkers can then be used to assess activities and behaviors including eating specific foods or supplements, or combinations of activities to enhance these biomarkers in order to increase the placebo effect to improve the likelihood of a desired outcome. These "placebo effect biomarkers" may be also used as guidance for enhancement of an individual's belief, independently or in combination with other biomarker driven guides, or to guide individuals or vendors.

In another aspect, the present invention provides a database for storage of data on the biological phenotype, physiological phenotype, and behavioral and/or emotional phenotype. In some embodiments, the correlation between biological phenotype and behavioral and/or emotional phenotype and the correlation between biological/physiological phenotype and behavioral and/or emotional phenotype may also been stored in the database. Such database(s), which may include one or more collection(s) of related data organized for convenient access, preferably in a computer, of information about individuals are useful for a variety of purposes, including use by merchants in the prediction of buying behavior or to provide new information to users about their existing and potential future preferences.

The database may further comprise the identity of the sample from which a data point is generated. This may become important as certain molecules are only present in some of the samples. For example, the molecules present in urine are different from the molecules in sweat. There, the database may comprise the information identifying in which sample a molecule is present. Further, the correlation between the biological phenotype and behavioral and/or emotional phenotype may include the identity of the samples.

The database may also comprise the time at which the sample is collected from the subject. It is well known the human body activities, especially metabolisms, change over time and at different times in the same day. Thus, the composition of a sample may also vary during the day. It may be important for some embodiments to save the time of sample collection in the database in order to have this data available for correlation and analysis.

The database of the present invention may evolve as more data is added into the database, and the information in the database may also become more and more accurate and/or reliable over time due, for example, to the increase in the amount of data collected. As a result of this database evolution, new correlations may be established and new ways of providing guidance to an individual may become possible. For example, uploaded biomarker data from an individual may be correlated with a map location, i.e., the location on map where the individual was when the biomarker data was measured or collected. Based on this relationship, and with more data and information available, the present invention may further correlate the map location with other information, such as environmental factors (such as pollen counts, UV intensity, etc). Therefore, the evolved database may generate or include correlations from biomarkers to map location and environmental factors. In other words, different biomarkers may be correlated with different environmental factors. For example, a biomarker may be correlated with pollen count as "pollen biomarker." Another biomarker may be correlated with sunlight as "sunlight biomarker."

The database may evolve even further as more new, different data are added to the database. For example, the sunlight biomarker(s) might be correlated to different data such as an increase in purchasing. In one embodiment, if the system detects sunlight biomarker(s) in a sample from an individual, the system can then recommend to the individual who does not want to over-purchase to eat foods or supplements that are known to decrease the sunlight biomarker(s), or it can recommend to advertisers to sell to the individual food or supplements that decrease the sunlight biomarker(s).

Many examples of data collection and storage for analysis already exist. For example, HLA (human leukocyte antigen) typing databases collect and store information about the HLA type of individuals.

Biological phenotypic analysis can be performed on a number of individuals in different emotional states, e.g. perhaps 5, 10, 20, 25 or 100 people per emotional state, to initially establish the database. Data is collected, and a database is generated which correlates biological phenotype with behavioral and/or emotional phenotype from the answers to the questions. Over time, the database can be modified to eliminate behavioral data not correlated with biological phenotype. Data can be continually collected, and the database evolved. Behavioral and/or emotional phenotype matches with biological phenotype can be ranked, and the ranking can be modified, or evolved, over time as new information is input into the database. It is contemplated that new behavioral and emotional information and biological phenotype information can be continually integrated into the database over time and that this information can be employed to reevaluate, modify, change or update various correlations.

In one method of the present invention, biological phenotypic assessment is a fundamental aspect of a correlation to behavior or emotion in order to derive a meaningful or valid "emotype," or a temporal biologic condition or state correlation with behavior and emotion that allows assessment and prediction of current and future behavior.

After the correlations between biological phenotype and behavioral and/or emotional phenotype have been established, these correlations may then be used as "rules" to predict future behaviors or emotional states for an individual or group of individuals. For example, if the presence of a polypeptide A and a metabolite B in saliva is correlated with tendency of liking chocolate (a "rule"), then if the polypeptide A and metabolite B are detected in a person's saliva, it may be predicted that the person is in a state of wanting to consume chocolate. In this hypothetical example, a product recommendation for chocolate may be sent to the person through, for example, a mobile device in response to the data.

These "rules" may also be used to alter an individual's living environment. For example, if the presence of a particular metabolite X in urine is correlated with a sad emotion. When an individual uses a toilet which is equipped with a sensor to detect metabolite X and it is found that the urine of that individual has metabolite X, then a signal may be sent, through a wire or wirelessly, to adjust the brightness and color of lighting in the environment in order to cheer up the individual.

In the method of the present invention, decision making and data search results may be linked to a user's biological phenotype to yield information and patterns that are useful in a variety of applications. This biological integration into data search can contribute to lowering the high error rate of search efficiency and speed. The marker used to measure the biomolecular state of the individual, such as proteins, that are always present or always absent can be predictive of future behavior since their presence or absence will be correlated with responses to questions.

In another embodiment, the present invention is a method for predicting consumer behavior comprising: using a processing device; obtaining a sample comprising biological molecules from a consumer; simultaneously or at another time obtaining survey data from the consumer; storing the survey data in a survey database; analyzing the sample of biological molecules to determine the composition of biological molecules; storing the data from the composition in a sample database; correlating the data from the sample database to the data from the survey database; and using the correlated data to predict consumer behavior using the processing device.

In yet another embodiment, the present invention is a method for predicting an individual's behavior or preferences, the method comprising: obtaining a sample comprising biological molecules from an individual, simultaneously or at another time obtaining survey data from the individual; storing the survey data in a survey database; analyzing the sample of biological molecules to determine the composition of biological molecules; storing the data from the composition in a sample database; correlating the data from the sample database to the data from the survey database; and predicting behavior or preference based on the correlation between the biological data in the sample database and the survey data in the survey database.

In yet another embodiment, the present invention is a method for predicting an individual's behavior or preferences, the method comprising: obtaining a sample comprising biological molecules from an individual; analyzing the sample of biological molecules to determine the composition of biological molecules; correlating the data from the sample to the data from a survey database; and predicting behavior or preference based on the correlation between the biological data in the sample and the survey data in the survey database.

The biological molecules referred to in the above-mentioned paragraphs may include, but are not limited to, the various items described above which may be detected in, isolated from or quantified in a sample.

In another embodiment, the present invention is a method for correlating data from a previously generated sample database and a previously generated survey database comprising: correlating data from the sample database to the data from the survey database. In another embodiment, the present invention is a method for correlating data from a sample database and a survey database comprising: obtaining a sample comprising biological molecules from an individual, analyzing the sample of biological molecules to determine the composition of biological molecules; and correlating the data from the sample database to the data from a survey database.

In another embodiment, the present invention is a method for predicting one or more individual's behavior or preferences, the method comprising: obtaining samples comprising biological molecules from one or more individuals; analyzing the samples of biological molecules to determine the composition of biological molecules; storing the data from the composition in a sample database; correlating the data from the sample database to the data from a survey database; predicting behavior or preference based on the correlation between the biological data in the sample database and the survey data in the survey database.

In one aspect of the present invention, after proteins are measured in a sample, genes encoding such proteins can be determined. It is then possible to use a surrogate polynucleotide (such as DNA or RNA) assay to measure the biomolecular state of the individual. The reverse process of measuring proteins first, followed by use of a nucleic acid as a surrogate for determination of a biomolecular state of an individual, has not been pursued at scale. One reason may be the belief that nucleic acid measurement is optimal for determining the biomolecular state of an individual, and another reason may be the higher cost of protein assays versus nucleic acid assays. Thus, in another embodiment of the present invention, proteins are first measured, followed by determination of corresponding DNA or RNA molecules, and such nucleic acid molecules are then assayed to measure the biomolecular state of an individual.

It is desirable in the methods of the present invention to measure proteins. Measurement of proteins in the methods of the present invention allows for the distinction between human proteins in the body and proteins from microbes present in the body.

Individuals include consumers in the methods of the present invention. Databases include information from a plurality of individuals.

The methods of the present invention are useful in the several applications where demonstration or prediction of the affinity of individuals for anything (for example people, electronic gadgets, music, food, fashion, games, books, and consumables, and the like) is useful. For example dating services, pet services and supplies (pets biomolecular state can be measured and owners, for example, can provide information about behavior states), the political system (to provide information about voting choices), and the travel industry (marketing for vacation locations) will find the information provided by the database to be useful for correlating biomolecular states with individuals behavior (for example, choices).

A method for correlating data from a sample database and a survey database comprising: obtaining a sample comprising biological molecules from an individual, simultaneously obtaining survey data from the individual; storing the survey data in a survey database; analyzing the sample of biological molecules to determine the composition of biological molecules; storing the data from the composition in a sample database; correlating the data from the sample database to the data from the survey database.

The sample is selected from urine or stool, blood, an individual's breath, human cells, hair or fingernails, saliva, mucus or tears. The biological molecule is selected from a protein, a small molecule, a metabolite, a peptide, a hormone, a nucleic acid, and combinations thereof. The individual may be a consumer. The analysis of the sample is performed using a mass spectrometer or other assay. The survey optionally comprises data from a physiological measurement. The physiological measurement is heart rate, galvanic response, body temperature or pupil dilation. The survey comprises questions about behavior, preferences, mood, senses or sensation, which may be completed by a consumer or a person familiar with the consumer.

The correlated data may be is used to predict consumer behavior, or consumer behavior for targeted advertising.

The method may further comprise obtaining a sample comprising biological molecules from a second individual, simultaneously obtaining survey data from the second individual; storing the new survey data from the second individual in the survey database to create an updated survey database; analyzing the sample of biological molecules from the second individual to determine the second composition of biological molecules; storing the data from the second composition in the sample database to create an updated sample database; correlating the data from the updated sample database to the data from the updated survey database.

The method may further comprise obtaining a sample comprising biological molecules from a third and more individuals, simultaneously obtaining survey data from the third and more individuals; storing the new survey data from the third and more individuals in the survey database to create an updated survey database; analyzing the sample of biological molecules from the third and more individuals to determine the third and more compositions of biological molecules; storing the data from the third and more compositions in the sample database to create an updated sample database; correlating the data from the updated sample database to the data from the updated survey database.

The databases evolve based on additional data from new individuals.

A method for predicting consumer behavior comprising: using a processing device; obtaining a sample comprising biological molecules from a consumer; simultaneously obtaining survey data from the consumer; storing the survey data in a survey database; analyzing the sample of biological molecules to determine the composition of biological molecules; storing the data from the composition in a sample database; correlating the data from the sample database to the data from the survey database; using the correlated data to predict consumer behavior using the processing device.

The databases comprise data from a plurality of consumers. The processing device may be a computer or a mobile phone.

A method for predicting an individual's behavior or preferences, the method comprising: obtaining a sample comprising biological molecules from an individual, simultaneously obtaining survey data from the individual; storing the survey data in a survey database; analyzing the sample of biological molecules to determine the composition of biological molecules; storing the data from the composition in a sample database; correlating the data from the sample database to the data from the survey database; predicting behavior or preference based on the correlation between the biological data in the sample database and the survey data in the survey database.

The databases comprise data from a plurality of individuals, which may be consumers.

A method for predicting an individual's behavior or preferences, the method comprising: obtaining a sample comprising biological molecules from an individual; analyzing the sample of biological molecules to determine the composition of biological molecules; correlating the data from the sample to the data from a survey database; predicting behavior or preference based on the correlation between the biological data in the sample and the survey data in the survey database.

A method for correlating data from a previously generated sample database and a previously generated survey database comprising: correlating data from the sample database to the data from the survey database.

A method for correlating data from a sample database and a survey database comprising: obtaining a sample comprising biological molecules from an individual, analyzing the sample of biological molecules to determine the composition of biological molecules; correlating the data from the sample database to the data from a survey database.

The correlated data reveals a behavior.

A method for predicting one or more individual's behavior or preferences, the method comprising: obtaining samples comprising biological molecules from one or more individuals; analyzing the samples of biological molecules to determine the composition of biological molecules; storing the data from the composition in a sample database; correlating the data from the sample database to the data from a survey database; predicting behavior or preference based on the correlation between the biological data in the sample database and the survey data in the survey database.

A method wherein the correlated data is provided as information to a product provider or a service provider for use in promotion and/or selling of products or services.

A method wherein the correlated data is provided as information to product provider and/or a service provider and used in grading or rating of business, products or services, for example a rating (for example of 1, 2, 3 or more levels) of quality or utility for a particular group of individuals.

A method wherein the correlated data is provided as information to a product providers or a service provider, and whereby they product provider or service provider uses the data provide feedback or guidance to individuals, including consumers.

A method wherein the correlated data is provided as information to individuals such as consumers to provide feedback or guidance to the individuals.

The following references are incorporated entirely herein by reference:

De Ruiter, J. R. (2004), 'Genetic markers in primate studies: elucidating behavior and its evolution', *International journal of primatology*, 25 (5). pp. 1173-1189.

Publication entitled: Opportunities in Neuroscience for Future Army Applications (2009) Board on Army Science and Technology (BAST), Committee on Opportunities in Neuroscience for Future Army Applications; Division on Engineering and Physical Sciences; NATIONAL RESEARCH COUNCIL OF THE NATIONAL ACADEMIES, THE NATIONAL ACADEMIES PRESS, Washington, D.C. www.nap.edu Goldsmith et al., Vol. 5, No. 7, 5408-5416, 2011, *ACS Nano*; Published online Jun. 22, 2011.

Samuel M. Khamis, et al., Homo-DNA Functionalized Carbon Nanotube Chemical Sensors, Journal of Physics and Chemistry of Solids 71 (2010) 476-479.

S. M. Khamis, et al., DNA-decorated carbon nanotube-based FETs as ultrasensitive chemical sensors: Discrimination of homologues, structural isomers, and optical isomers, AIP Advances 2, 022110 (2012); doi: 10.1063/1.4705394

Yian-Biao Zhang, et al., Functionalized Carbon Nanotubes for Detecting Viral Proteins, Nano Letters, 2007 Vol. 7, No. 10 3086-3091

Without further elaboration, it is believed that one skilled in the art can, using the preceding description, utilize the present invention to its fullest extent.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A database comprising information identifying a plurality of human subjects, data on biological phenotype of the plurality of subjects, survey-based data on behavioral and/or emotional phenotype of the plurality of subjects, and correlations between the data on biological phenotype from the plurality of subjects and the survey-based data on behavioral and/or emotional phenotype from the plurality of subjects,
    wherein the data on biological phenotype is collected from a plurality of samples from the plurality of subjects,
    the survey-based data is collected from answers to social behavioral and emotional questions from the plurality of subjects or from observations of the plurality of subjects by a third party, and
    the sample and the survey-based data are collected simultaneously so that a temporal biologic condition or state is correlated with behavior and/or emotion,
    wherein the database is configured to evolve when additional sample and survey-based data is added to the sample and survey-based data from the plurality of subjects by correlating the updated sample and survey-based data wherein the correlations are configured for use to provide feedback or guidance to the subject, to provide information to a product provider or a service provider for use in marketing and/or selling of products and/or services, to provide a product provider or service provider with information useful in grading or rating products or services, or to provide a product provider or service provider with information useful to design new and/or better products or services.

2. The database of claim 1, further comprising temporal location information for the subject, and wherein the temporal location information is collected simultaneously with the sample and survey-based data.

3. The database of claim 1, wherein the database is configured to continue to accept new data selected from the group consisting of data on biological phenotype of the subject, survey-based data on behavioral and/or emotional phenotype, data on map locations, and data on environmental factors.

4. The database of claim 3, wherein the database is configured to evolve to include at least one new correlation based on new data that is accepted.

* * * * *